United States Patent [19]

Yohe et al.

[11] Patent Number: 4,631,961

[45] Date of Patent: Dec. 30, 1986

[54] SAMPLING DEVICE FOR DETERMINING CONDITIONS ON THE INTERIOR SURFACE OF A WATER MAIN

[75] Inventors: Thomas L. Yohe, West Chester; Rodney M. Donlan, Ardmore; Karl M. Kyriss, West Chester, all of Pa.

[73] Assignee: Philadelphia Suburban Water Company, Bryn Mawr, Pa.

[21] Appl. No.: 815,407

[22] Filed: Dec. 31, 1985

[51] Int. Cl.$^4$ .............................................. G01N 17/00
[52] U.S. Cl. .............................. 73/866.5; 73/863.85; 73/86; 422/53; 324/65 CR
[58] Field of Search .......... 73/863.85, 863.86, 863.82, 73/86, 432 B, 432 R, 432 J; 422/53; 324/65 CR, 65 P, 71.2, 437, 445, 446, 447, 448, 449, 450, 425–436, 438–444

[56] References Cited

U.S. PATENT DOCUMENTS

| | | | |
|---|---|---|---|
| 2,091,613 | 8/1937 | Polston | 73/863.85 X |
| 2,756,129 | 7/1956 | Harris | 422/53 |
| 2,982,930 | 5/1961 | Wygant | 73/86 X |
| 3,155,933 | 11/1964 | Rohrback et al. | 324/65 CR |
| 3,980,542 | 9/1976 | Winslow, Jr. et al. | 73/86 X |
| 4,142,402 | 3/1979 | Mattioli et al. | 422/53 X |
| 4,275,592 | 6/1981 | Atwood et al. | 73/86 X |
| 4,294,124 | 10/1981 | Kalwaitis | 73/863.85 |
| 4,367,440 | 1/1983 | Mazzagatti | 324/445 |
| 4,437,090 | 3/1984 | Hanson | 177/50 X |
| 4,537,071 | 8/1985 | Waterman | 73/432 B |

FOREIGN PATENT DOCUMENTS

| | | | |
|---|---|---|---|
| 2308570 | 8/1973 | Fed. Rep. of Germany | 73/86 |
| 595475 | 12/1947 | United Kingdom | 324/448 |

OTHER PUBLICATIONS

Capital Controls Company Drawing Dated Mar. 31, 1967, Entitled "1 inch Corp. Cock Assembly".
Bean, E. L., *Progress Report on Water Quality Criteria*, Journal American Water Works Association, vol. 54, Nov. 1962, pp. 1313, 1322, 1329–1330.

*Primary Examiner*—Stewart J. Levy
*Assistant Examiner*—Tom Noland
*Attorney, Agent, or Firm*—Howson and Howson

[57] ABSTRACT

A probe rod is inserted into a water main through a corporation cock. The rod has a plurality of transverse passages parallel to one another and aligned in the direction of flow. Within these transverse passages, in flush relationship to the passage walls, are inserted removable sampling rings. All but one of the rings are of the same material as the inner wall of the main. The remaining ring, used as a control, is a synthetic resin ring. The flush relationship prevents the formation of turbulent eddies at the ends of the rings. Consequently, microbial growth conditions on the rings themselves reliably simulate conditions on the interior wall of the main.

Within a tubular extension on the exterior of the corporation cock an O-ring seal is provided. The length of the extension, and the position of the seal, are such that the probe rod can be partially withdrawn beyond the corporation valve without causing any of the transverse passages to pass through the O-ring. Thus, the rod can be partially withdrawn, and the corporation valve closed before the rod is fully withdrawn. Because of the length of the extension and the position of the O-ring, partial withdrawal of the probe rod can be accomplished without scouring of the sampling rings due to high velocity flow of water through the transverse passages as they move through the O-ring.

19 Claims, 4 Drawing Figures

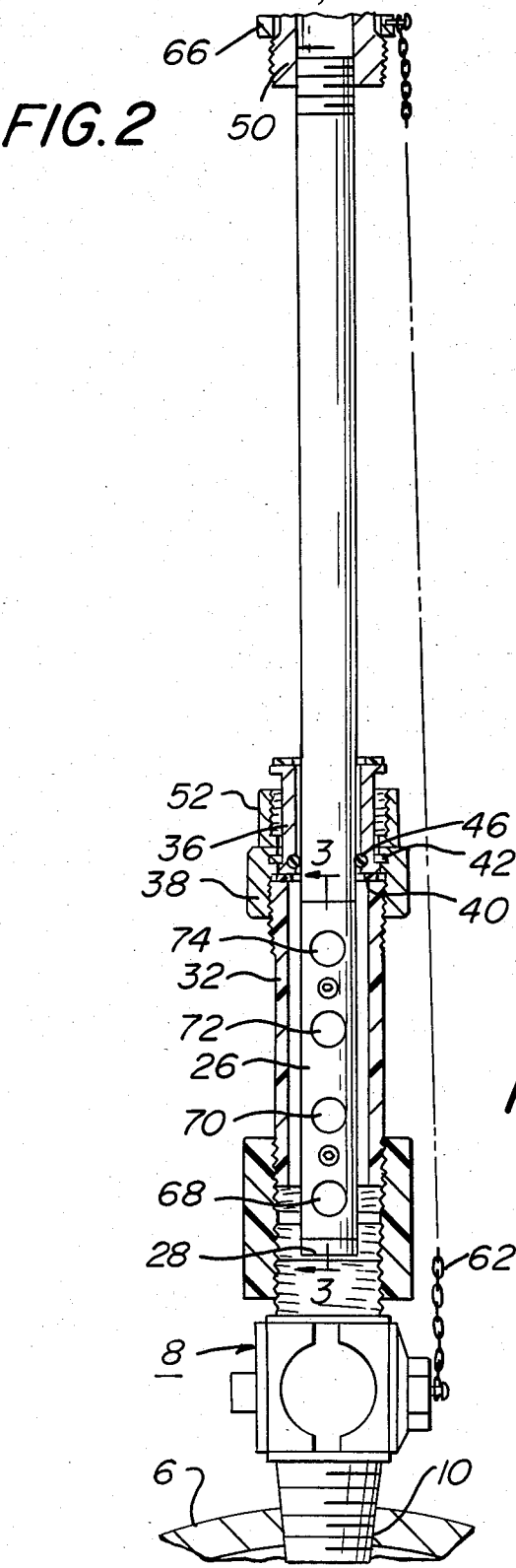
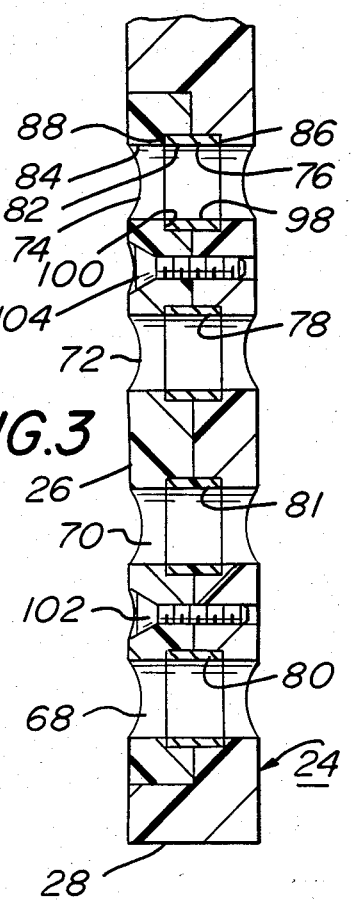
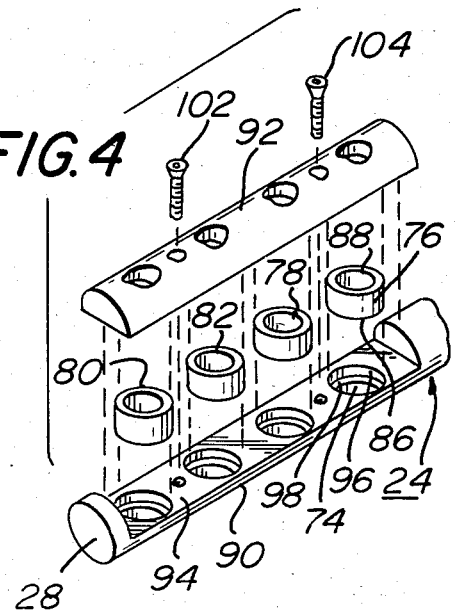

SAMPLING DEVICE FOR DETERMINING CONDITIONS ON THE INTERIOR SURFACE OF A WATER MAIN

BRIEF SUMMARY OF THE INVENTION

This invention relates to the determination of conditions on the interior surface of a main in a water supply system, and more specifically to a novel sampling device for insertion into a water main, which reliably indicates conditions on the interior surface of the main without requiring disassembly or destruction of the main, and without necessitating discontinuation of service.

The invention has particular utility in the determination of conditions of microbial growth on the interior wall of a water main, but can also be used for determining the extent of corrosion of the interior wall of the water main.

Water utilities constantly monitor and analyze the drinking water which they supply for microbial and chemical content. It is also desirable to monitor conditions of microbial growth on the interior walls of water mains. However, it is not practical to shut down service for the removal and replacement of sections of a water main so that the interior wall of the removed section can be examined.

The general object of this invention is to provide a practical and reliable solution to the problem of monitoring microbial growth conditions on the interior wall of a water main.

In accordance with the invention, a probe in the form of a rod is inserted into a water main through a corporation cock. The rod has a plurality of transverse passages which are parallel to one another and aligned in the direction of flow of water through the main. Within these transverse passages, in flush relationship to the passage walls, are inserted removable sampling rings. Preferably, but not necessarily, all but one of the rings are of the same material as the inner wall of the main. An additional synthetic resin ring may be used as a control. With the rings in flush relationship with the transverse passages in the probe rod, the formation of turbulent eddies at the ends of the rings is avoided. Consequently, the microbial growth conditions on the rings themselves reliably simulate conditions on the interior wall of the main.

A tubular extension is provided on the exterior of the corporation cock, and within the tubular extension, a seal, preferably an O-ring, is provided. The length of the extension, and the position of the seal, are such that the probe rod can be partially withdrawn beyond the valve within the corporation cock without causing any of the transverse passages to pass through the seal. Thus, the rod can be partially withdrawn, and the corporation cock closed before the rod is fully withdrawn. Because of the length of the extension and the position of the seal, partial withdrawal of the probe rod can be accomplished without scouring of the sampling rings due to high velocity flow of water through the transverse passage as they move through the seal. Such high velocity flow would cause the microbial growth to break away from the rings, rendering them useless as indicators of conditions on the inner wall of the water main.

Thus, it is a further object of the invention to provide a sampling device which accurately simulates conditions on the inner wall of a water main, and in which the simulated conditions are not destroyed when the probe is removed.

Various other objects of the invention will be apparent from the following detailed description when read in conjunction with the drawings.

BRIEF DESCRIPTION OF THE DRAWINGS

FIG. 2 is a fragmentary section showing the rod of the sampling device in its partially withdrawn condition;

FIG. 3 is a longitudinal section through the working end of the sampling rod, showing the transverse passages, and the rings in flush relationship in the passages; and FIG. 4 is a fragmentary exploded perspective view of the working end of the probe rod, illustrating how the rings are removed and replaced.

DETAILED DESCRIPTION

Figure 1:
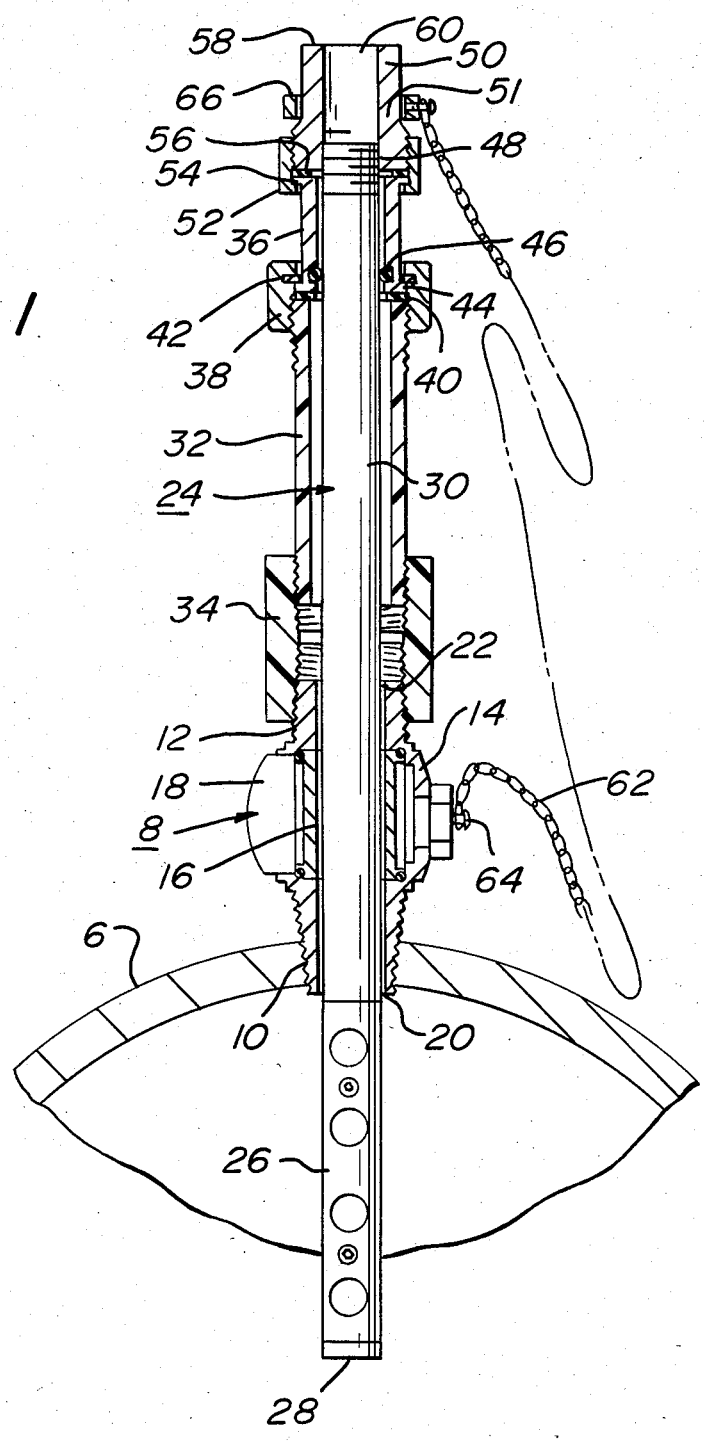
FIG. 1 is a fragmentary sectional view showing the sampling device fully inserted into the interior of a water main.

FIG. 1 shows a water main 6, which is typically of steel or cast iron and at least six inches in internal diameter. A corporation cock 8 has a threaded section 10 threaded into an opening through the wall of the main. The corporation cock also has a threaded section 12 on the opposite side of its body 14. Within the body 14 is a rotatable valve element 16 connected to a manual or wrench-operable projection 18. Opening 20 at one end of the corporation cock, and opening 22 at the other end, are connected by a straight passage when valve element 16 is open, as shown.

An elongated cylindrical probe rod 24, preferably of polyvinyl chloride or similar rigid synthetic resin, has a first section 26 extending beyond opening 20 of the corporation cock into the interior of main 6. The rod terminates, within the interior of the main, at rod end 28. Rod 24 also has a second section 30 extending exteriorly beyond opening 22 of the corporation valve. Section 30 extends through extension tube 32, which is secured to threaded section 12 of the corporation valve by an internally threaded collar 34. A second extension tube 36 is secured to the upper end of extension tube 32 by a clamping collar 38. A gasket 40 is provided between the adjacent end faces of tubes 32 and 36. Clamping collar 38 is provided with an internal split ring 42, which engages a flange 44 when collar 38 is tightened onto threads at the upper end of tubular extension 32. Tubular extensions 32 and 36 together provide an elongated extension of the passage in the corporation cock. A sealing O-ring 46 is provided in a groove formed on the interior wall of extension tube 36. The O-ring is preferably of neoprene or similar elastomeric material, and conforms to the cross-section of tube 30 to provide a fluid-tight seal capable of withstanding the pressure of water within the main. The pressure is usually less than 100 psi. in typical systems but can approach, and even exceed 100 psi. in some systems.

The upper end of rod 30 is threaded at 48. These threads mate with internal threads in adapter 50 at the upper end of the rod. Adapter 50 has external threads, and is removably secured to tubular extension 36 by a threaded collar 52, which engages flange 54 formed on the upper end of extension 36. A gasket 56 is clamped between the upper end face of tubular extension 36, and the lower end face of adapter 50. The upper end face 58 of adapter 50 is provided with an opening 60, which forms a recess in face 58. The purpose of this recess is to allow for pushing of the probe rod by means of a broomstick or similar tool.

A safety chain 62 is attached by means of screw 64 to the corporation cock at one end, and to a ring 66 at its other end. Ring 66 surrounds adapter 50, the lower threaded end 51 of which is larger than the internal diameter of ring 66. Chain 62 thus limits the extent to which pressure of the water in the main can force the probe rod outward when collar 52 is disengaged from adapter 50.

Referring now to FIG. 3, the first section 26 of the elongated cylindrical probe rod has formed in it a series of parallel transverse passages 68, 70, 72 and 74. When the rod is in place within the main, as shown in FIG. 4, these passages are at different radial locations within the main so that flow variations within the main can be taken into account. Metal rings 76, 78 and 80 are seated in transverse passages 74, 72 and 68 respectively. The rings have coaxial cylindrical inner and outer walls and annular end faces perpendicular to the ring axes. The metal rings are preferably made from the same material as that of the main, or of the inner wall of the main in the event that the main consists of more than one material. A similarly shaped synthetic resin ring 81 is seated in transverse passage 70.

Ring 76 is situated in a recess formed in the wall of transverse passage 74 and spaced from the ends of the passage. Inner wall 82 of the ring is flush with the inner wall 84 of the passage. The length of the ring is substantially equal to the length of the recess so that end faces 86 and 88 of the ring respectively abut annular faces 98 and 100 of the recess. Consequently, with the ring in place within the passage, the passage is substantially smooth, and the formation of turbulent eddies at the ends of the ring is substantially prevented. The conditions within the ring itself simulate the flow conditions along the walls of the water main. The remaining rings 78, 81 and 80 are similarly situated in flush relationship with passages 72, 70 and 68.

As shown in FIG. 4, the portion of the probe rod having the transverse passages is split longitudinally into two parts 90 and 92. Part 90 is an integral part of the remainder of the rod, whereas part 92 is separable from part 90. The split is preferably situated along the plane of face 94, which is parallel to the length of rod 24, through the central axis of the rod, and perpendicular to the axes of the transverse passages. Furthermore, the plane intersects the recesses of the transverse passages so that, when part 92 is temporarily removed from part 90, the rings can be set in place. Thus, as shown in FIG. 4, ring 76 can be set in place in passage 74, with its annular end face 86 in contact with face 98 of the recess, and with its cylindrical outer surface in contact with cylindrical wall 96 of the recess. The portion of passage 74 within the removable part of the rod is similarly configured, as shown in FIG. 3. Part 92 is held in place against part 90 of the rod by screws 102 and 104.

After a period of exposure of the rings to the conditions within the main, the probe rod can be partially withdrawn to the position depicted in FIG. 2, in which end 28 of the rod is located on the exterior side of the valve element in the corporation cock so that the valve element can be closed, and in which transverse openings 68–74 are all located between the valve element of the corporation cock and seal 46. The rod is brought to this condition by disengaging threaded collar 52 from the threads of adapter 50 while exerting a manual pressure on adapter 50 through a broomstick or similar tool, and then slowly releasing pressure on the broomstick, allowing water pressure to force the rod upwardly until chain 52 becomes taut. The length of chain 62 is such as to limit upward movement of the rod until it reaches the condition depicted in FIG. 2. Preferably, the length of the chain and the position of seal 46 are such that the rod can be withdrawn until the chain becomes taut, the valve of the corporation cock can then be closed, and the rod then moved downwardly a short distance toward the closed valve element so that ring 66 can be removed from adapter 50, allowing complete withdrawal of the rod.

Operation of the apparatus just described takes place as follows. First, a new set of rings is installed in the end of the probe rod in the manner depicted in FIG. 4. Preferably, three rings of the same material as the main are used along with one synthetic resin ring provided as a control. The synthetic resin ring, being non-corrodable, makes it possible to evaluate the effect of corrosion on the microbial population. The position of the synthetic resin ring is not critical. It can be in any one of the transverse passages of the rod. With the rings in place, and the separable elements 90 and 92 of the rod secured together as shown in FIG. 3, the rod is inserted inwardly toward the corporation cock through the extension tubes, and ring 66 on safety chain 62 set in place as shown in FIG. 2. The rod is manually urged in the outward direction so that the chain remains taut while the valve of the corporation cock is opened. When the valve is opened, pressure from the main urges the rod outwardly, and maintains the chain in a taut condition. The rod is then urged downwardly, and collar 52 is threaded onto adapter 50 to lock the rod in place. Suitable markings (not shown) are preferably provided on the rod or on the adapter to enable the user to insure that the transverse openings 68 and 74 are aligned with the axis of the water main, and thus with the direction of water flow therein.

The corporation cock and extension assembly are typically located within a narrow manhole capable of accommodating only one person. Thus, it is convenient to have one person push downwardly on the rod with a broomstick from the exterior of the manhole, while another person within the manhole engages or disengages threaded collar 52, attaches or detaches the chain, and opens or closes the valve element of the corporation cock.

After a sufficient period of time to allow for microbial growth on the rings, the rod is partially withdrawn, the valve is closed, and then the rod is fully withdrawn so that the rings can be removed and inspected. The rings not only give an indication of microbial growth on the interior of the main, but also indicate the rate of corrosion of the main.

The rings, particularly because of their flush relationship with the transverse passages of the probe rod, allow for microbial growth which accurately simulates conditions on the interior wall of the water main. The length of the extension and the position of the seal 46 therein are such as to allow partial withdrawal of the rod, and closure of the corporation valve before the transverse openings reach the location of the seal. Thus, scouring of the rings by high velocity flow of escaping water upon removal of the rod is prevented.

Many variations of the apparatus just described can be made. For example, the number of rings, as well as the sizes thereof can be varied. Likewise, although threaded collar 52 is desirable for locking the probe rod in place within the main, various alternative locking means can be used. Many other variations in the apparatus described can be made without departing from the scope of the invention as defined in the following claims.

We claim:

1. In a water supply system comprising a pressurized water main, a sampling device for determining conditions on the interior surface of the main comprising:

closable access means providing access to the interior of the main;

a rod extendable into the interior of the water main through said closable access means;

said closable access means including means for preventing the escape of water from the interior of the main through said access means when the rod extends into the interior of the main; and means for removably securing said rod to the main whereby pressure within the interior of the water main is prevented from forcing the rod out of the position in which it extends into the interior of the water main;

wherein said rod has a transverse passage and a ring removably held in said transverse passage, the rod being positionable, when extended into the interior of the main, so that the transverse passage extends parallel to the direction of water flow in the main.

2. A sampling device according to claim 1 in which the ring is of the same material as the inner wall of the main.

3. A sampling device according to claim 1 in which said ring has a cylindrical inner wall, in which said transverse passage has a wall with an annular recess spaced from both ends thereof and cylindrical unrecessed parts located on both sides of the recess, and in which said ring is located in said annular recess, the diameter of the inner wall of the ring being substantially equal to the diameter of the cylindrical unrecessed parts of the wall of the transverse passage and the axial length of the ring being substantially equal to the length of the recess whereby the ring is in flush relationship with the transverse passage and the formation of eddies at the ends of the ring is prevented.

4. A sampling device according to claim 3 in which the ring is of the same material as the inner wall of the main.

5. A sampling device according to claim 1 in which said rod has a plurality of transverse passages extending parallel to one another, and a plurality of rings, there being one ring removably held in each of said transverse passages, the rod being positionable, when extended into the interior of the main, so that the parallel transverse passages extend parallel to the direction of water flow in the main.

6. A sampling device according to claim 5 in which at least all but one of said rings is of the same material as the inner wall of the main.

7. A sampling device according to claim 5 in which each of the rings has a cylindrical inner wall, in which each of said transverse passages has a wall with an annular recess spaced from both ends thereof and cylindrical unrecessed parts located on both sides of the recess, and in which each of said rings is located in one of said annular recesses, the diameter of the inner wall of each ring being substantially equal to the diameter of the cylindrical unrecessed parts of the wall of the transverse passage in the recess of which it is located, and the axial length of each ring being substantially equal to the length of the recess in which it is located, whereby the ring is in flush relationship with the transverse passage in the recess of which it is located and the formation of eddies at the ends of the rings is prevented.

8. A sampling device according to claim 7 in which at least all but one of said rings is of the same material as the inner wall of the main.

9. In a water supply system comprising a pressurized water main having a central axis, a sampling device for determining conditions on the interior surface of the main comprising:

a corporation cock connected to the wall of the water main and having a first opening in communication with the interior of the main, a second opening outside the main, and valve means selectably operable to open and close off communication between said first and second openings, the first and second openings, and the valve means, when opened, together providing a substantially straight passage extending in a direction substantially perpendicular to the water main axis;

an elongated cylindrical rod extendable through said substantially straight passage of the corporation cock into the interior of the water main, the rod having a first section, adjacent one end thereof, located within the water main, and a second section extendable outwardly from the second opening of the corporation cock;

extension means connected to the corporation cock at the second opening thereof, and providing an extension passage communicating with, and aligned with, said substantially straight passage of the corporation valve, the extension passage having sealing means conforming to the cross-sectional shape of the cylindrical rod whereby the rod can slide through said straight passage of the corporation cock and through said extension passage but water from the main is substantially completely prevented from escaping through the space between the rod and said conforming portion of the extension passage; and means for removably securing said rod to the extension means whereby pressure within the interior of the water main is prevented from forcing the rod out of the position in which its first section is located within the water main;

wherein said first section of the elongated cylindrical rod has a plurality of transverse passages extending parallel to one another and in perpendicular relationship to the direction of elongation of the rod, and a plurality of rings, there being one ring removably held in each of said transverse passages, the rod being positionable so that the transverse passages extend parallel to the central axis of the water main.

10. A sampling device according to claim 9 in which each of the rings has a cylindrical inner wall, in which each of said transverse passages has a wall with an annular recess spaced from both ends thereof and cylindrical unrecessed parts located on both sides of the recess, and in which each of said rings is located in one of said annular recesses, the diameter of the inner wall of each ring being substantially equal to the diameter of the cylindrical unrecessed parts of the wall of the transverse passage in the recess of which it is located, and the axial length of each ring being substantially equal to the length of the recess in which it is located, whereby the ring is in flush relationship with the transverse passage in the recess of which it is located and the formation of eddies at the ends of the rings is prevented.

11. A sampling device according to claim 10 in which said elongated cylindrical rod is split into two parts, along a plane parallel to the direction of elongation of the rod and intersecting said recesses of the transverse passages, at least through the length of the portion of the rod having said transverse passages, the two parts being separable from each other to allow removal of the rings, and having means for removably securing said two parts together.

12. A samping device according to claim 9 in which the extension passage is sufficiently long, and the sealing means is so positioned therein, that the portion of the rod having said transverse passages and including said one end thereof can, upon partial withdrawal of the rod, be located between the valve means of the corporation cock and said sealing means.

13. A sampling device according to claim 12 in which the sealing means is a sealing ring located in a groove in the wall of the extension passage.

14. A sampling device according to claim 12 including limiting means for preventing withdrawal of said rod beyond the position in which all of the transverse passages are located between the valve means of the corporation cock and said sealing means.

15. A sampling device according to claim 9 in which the face of the end of the elongated cylindrical rod opposite said one end has a recess.

16. A sampling device according to claim 9 in which at least one of said rings is of the same material as the inner wall of the water main.

17. A sampling device according to claim 9 in which at least all but one of said rings are of the same material as the inner wall of the water main.

18. A sampling device according to claim 17 in which one of the rings is of a synthetic resin material and the remaining rings and the interior wall of the water main are of metal.

19. In a water supply system comprising a pressurized water main having a central axis, a sampling device for determining conditions on the interior surface of the main comprising:

a corporation cock connected to the wall of the water main and having a first opening in communication with the interior of the main, a second opening outside the main, and valve means selectably operable to open and close off communication between said first and second openings, the first and second openings and the valve means, when opened, together providing a substantially straight passage extending in a direction substantially perpendicular to the water main axis;

an elongated cylindrical rod extendable through said substantially straight passage of the corporation cock into the interior of the water main, the rod having a first section, adjacent one end thereof, located within the water main, and a second section extendable outwardly from the second opening of the corporation cock;

extension means connected to the corporation cock at the second opening thereof, and providing an extension passage communicating with, and aligned with, said substantially straight passage of the corporation valve, the extension passage having sealing means conforming to the cross-sectional shape of the cylindrical rod whereby the rod can slide through said straight passage of the corporation cock and through said extension passage but water from the main is substantially completely prevented from escaping through the space between the rod and said conforming portion of the extension passage; and means for removably securing said rod to the extension means whereby pressure within the interior of the water main is prevented from forcing the rod out of the position in which its first section is located within the water main;

wherein said first section of the elongated cylindrical rod has a plurality of transverse passages extending parallel to one another and in perpendicular relationship to the direction of elongation of the rod, and a plurality of rings, there being one ring removably held in each of said transverse passages, the rod being positionable so that the transverse passages extend parallel to the central axis of the water main;

in which each of the rings has a cylindrical inner wall, in which each of said transverse passages has a wall with an annular recess spaced from both ends thereof and cylindrical unrecessed parts located on both sides of the recess, and in which each of said rings is located in one of said annular recesses, the diameter of the inner wall of each ring being substantially equal to the diameter of the cylindrical unrecessed parts of the wall of the transverse passage in the recess of which it is located, and the axial length of each ring being substantially equal to the length of the recess in which it is located, whereby the ring is in flush relationship with the transverse passage in the recess of which it is located and the formation of eddies at the ends of the rings is prevented;

in which said elongated cylindrical rod is split into two parts, along a plane parallel to the direction of elongation of the rod and intersecting said recesses of the transverse passages, at least through the length of the portion of the rod having said transverse passages, the two parts being separable from each other to allow removal of the rings, and having means for removably securing said two parts together;

in which the extension passage is sufficiently long, and the sealing means is so positioned therein, that the portion of the rod having said transverse passages and including said one end thereof can, upon partial withdrawal of the rod, be located between the valve means of the corporation cock and said sealing means;

in which the sealing means is a sealing ring located in a groove in the wall of the extension passage;

including limiting means for preventing withdrawal of said rod beyond the position in which all of the transverse passages are located between the valve means of the corporation cock and said sealing means;

in which the face of the end of the elongated cylindrical rod opposite said one end has a recess;

in which all but one of said rings are of the same material as the inner wall of the water main; and in which said one of said rings is of a synthetic resin material and the remaining rings and the interior wall of the water main are of metal.

* * * * *